US012315262B2

(12) United States Patent
Santillo et al.

(10) Patent No.: US 12,315,262 B2
(45) Date of Patent: May 27, 2025

(54) GUEST MEASUREMENT SYSTEMS AND METHODS

(71) Applicant: Universal City Studios LLC, Universal City, CA (US)

(72) Inventors: Vincent Santillo, Orlando, FL (US); Cole Hirapara, Orlando, FL (US); Anthony Melo, Orlando, FL (US); Dionté Omar Henderson, Orlando, FL (US); Taylor Marceau, Bryson City, NC (US); Katarina Gosbee, Orlando, FL (US)

(73) Assignee: Universal City Studios LLC, Universal City, CA (US)

( * ) Notice: Subject to any disclaimer, the term of this patent is extended or adjusted under 35 U.S.C. 154(b) by 340 days.

(21) Appl. No.: 17/715,546

(22) Filed: Apr. 7, 2022

(65) Prior Publication Data

US 2022/0327838 A1    Oct. 13, 2022

Related U.S. Application Data

(60) Provisional application No. 63/172,442, filed on Apr. 8, 2021.

(51) Int. Cl.
*G06K 9/00*    (2022.01)
*G01S 17/08*    (2006.01)
(Continued)

(52) U.S. Cl.
CPC .............. *G06V 20/53* (2022.01); *G01S 17/08* (2013.01); *G01S 17/88* (2013.01); *G06T 7/60* (2013.01);
(Continued)

(58) Field of Classification Search
CPC .... G06V 20/53; G06V 10/761; G06V 40/107; G06V 20/52; G06V 40/10; G06V 40/103;
(Continued)

(56) References Cited

U.S. PATENT DOCUMENTS 8,210,955 B2 *    7/2012    Yule ...................... A63G 21/18
                                                      472/134
8,659,643 B2 *    2/2014    Purvis ...................... G06T 7/75
                                                      348/46
(Continued)

FOREIGN PATENT DOCUMENTS

CN         101038683 A  *  9/2007  ............. G06F 21/32
CN         102657532 A     9/2012
(Continued)

OTHER PUBLICATIONS

PCT/US2022/023897 International Search Report and Written Opinion mailed Jun. 27, 2022.
(Continued)

*Primary Examiner* — Shervin K Nakhjavan
(74) *Attorney, Agent, or Firm* — Fletcher Yoder, PC

(57) ABSTRACT

A guest measurement system includes a controller associated with an attraction measurement area of an individual attraction within a theme park. The guest measurement system includes a controller configured to receive sensor signals indicative of guest characteristics from one or more sensors. The controller includes a processor configured to detect one or more limbs of a guest based in part on the sensor signals, identify a plurality of subregions for an individual limb of the one or more limbs, estimate dimensions for the identified plurality of subregions for the individual limb, and generate a guest height calculation based on the estimated dimensions for the identified plurality of subregions.

21 Claims, 5 Drawing Sheets

(51) Int. Cl.
| | |
|---|---|
| *G01S 17/88* | (2006.01) |
| *G06T 7/60* | (2017.01) |
| *G06T 7/73* | (2017.01) |
| *G06V 10/74* | (2022.01) |
| *G06V 20/52* | (2022.01) |
| *G06V 40/10* | (2022.01) |
| *A63G 31/00* | (2006.01) |

(52) U.S. Cl.
CPC ............. *G06T 7/73* (2017.01); *G06V 10/761* (2022.01); *G06V 40/107* (2022.01); *A63G 31/00* (2013.01); *G06T 2207/30196* (2013.01); *G06T 2207/30232* (2013.01)

(58) Field of Classification Search
CPC .......... G01S 17/08; G01S 17/88; G01S 17/86; G06T 7/60; G06T 7/73; G06T 2207/30196; G06T 2207/30232; G06T 2207/20021; G06T 7/62; G06T 2207/10028; G06T 7/50; A63G 31/00; A61B 5/1072; A61B 5/1079; G01B 11/02
See application file for complete search history.

(56) References Cited

U.S. PATENT DOCUMENTS

| | | | | |
|---|---|---|---|---|
| 8,674,805 | B2* | 3/2014 | Charych | G07C 9/28 340/5.82 |
| 8,976,237 | B2 | 3/2015 | Cheng et al. | |
| 9,433,870 | B2* | 9/2016 | Blum | G06V 10/245 |
| 9,600,999 | B2* | 3/2017 | Stenzler | G08B 21/18 |
| 9,798,935 | B2* | 10/2017 | Sandahl | G06T 7/60 |
| 10,436,456 | B2* | 10/2019 | Park | F24F 11/77 |
| 10,643,085 | B1* | 5/2020 | Kim | G06V 20/593 |
| 10,674,941 | B2* | 6/2020 | Tanaka | A61B 5/1128 |
| 10,729,985 | B2 | 8/2020 | Stenzler et al. | |
| 10,824,878 | B2* | 11/2020 | Houri | G06V 20/53 |
| 10,825,196 | B2 | 11/2020 | Lin et al. | |
| 10,881,972 | B2* | 1/2021 | Mayfield | A63G 3/06 |
| 11,491,895 | B2* | 11/2022 | Mizoi | B60N 2/002 |
| 11,518,277 | B2* | 12/2022 | Bove | B60W 50/0098 |
| 11,625,859 | B2* | 4/2023 | Lee | G01B 11/2518 382/154 |
| 11,763,477 | B2* | 9/2023 | Veiga | G06T 7/73 382/103 |
| 11,769,387 | B2* | 9/2023 | Bar-Ilan | G06V 20/52 382/103 |
| 2015/0336014 | A1* | 11/2015 | Stenzler | G01J 1/0266 472/137 |
| 2018/0096490 | A1 | 4/2018 | Juvonen | |
| 2019/0162439 | A1* | 5/2019 | Tsuda | G01S 5/025 |
| 2019/0196577 | A1* | 6/2019 | Sronipah | G06F 3/0482 |
| 2019/0318491 | A1* | 10/2019 | Laganiere | G06T 7/521 |
| 2019/0357615 | A1 | 11/2019 | Koh et al. | |
| 2020/0405185 | A1 | 12/2020 | Ohashi | |
| 2021/0374431 | A1* | 12/2021 | Yim | G06T 7/60 |
| 2022/0306003 | A1* | 9/2022 | Morosawa | G06V 40/103 |
| 2022/0313115 | A1* | 10/2022 | Poulter | A61B 5/741 |
| 2023/0306776 | A1* | 9/2023 | Strauss | G06V 20/64 |

FOREIGN PATENT DOCUMENTS

| | | | | |
|---|---|---|---|---|
| CN | 108875701 A | * | 11/2018 | ............. G06V 40/10 |
| CN | 111012353 A | | 4/2020 | |
| CN | 111067530 A | * | 4/2020 | ........... A61B 5/1072 |
| CN | 111583334 B | * | 3/2023 | ............. G01C 11/02 |
| CN | 110226843 B | * | 5/2024 | ............. A47B 51/00 |
| EP | 2674914 A1 | * | 12/2013 | ......... G06K 9/00791 |
| JP | 2002045403 A | | 2/2002 | |
| JP | 2016185275 A | | 10/2016 | |
| KR | 20170007070 A | * | 1/2017 | ............... G06T 7/00 |
| KR | 20210030727 A | * | 3/2021 | ............. G06V 40/10 |
| WO | WO-2019060066 A1 | * | 3/2019 | ......... G06K 9/00255 |

OTHER PUBLICATIONS

Criminisi, Antonio et al.; "A New Approach to Obtain Height Measurements from Video," Proceedings of SPIE—The International Society for Optical Engineering, Jan. 2022.

Ljungberg, Jenny et al.; "Estimation of human height from surveillance camera footage—a reliability study," School of Health Science, Jonkoping University Department of Rehabilitation, May 2008.

* cited by examiner

GUEST MEASUREMENT SYSTEMS AND METHODS

CROSS-REFERENCE TO RELATED APPLICATIONS

This application claims priority to and the benefit of U.S. Provisional Application No. 63/172,442, filed Apr. 8, 2021, and entitled "GUEST MEASUREMENT SYSTEMS AND METHODS," the disclosure of which is incorporated by reference in its entirety for all purposes.

BACKGROUND

The present disclosure relates generally to the field of amusement parks. More specifically, embodiments of the present disclosure relate to methods and equipment utilized to measure guests in an amusement park to assess one or more physical characteristics and/or determine eligibility to enter an attraction of the amusement park, e.g., enter an amusement ride as a passenger.

Theme or amusement parks have become increasingly popular. More sophisticated and creative ride attractions have been helpful in increasing the popularity and success of such parks. Certain attractions may be height-restricted to passengers that are above a height threshold. For example, theme park ride attractions may involve ride vehicles, such as roller coaster type cars, or other vehicles that move along a ride path. Height restrictions for a ride may involve restricting the ride to passengers within a particular height range that can be fitted to the restraints of each seat. The passengers can be measured before entering the ride to determine if they fit within the height restrictions. For example, a passenger can manually compare their height to a line on the wall.

SUMMARY

Certain embodiments commensurate in scope with the originally claimed subject matter are summarized below. These embodiments are not intended to limit the scope of the disclosure, but rather these embodiments are intended only to provide a brief summary of certain disclosed embodiments. Indeed, the present disclosure may encompass a variety of forms that may be similar to or different from the embodiments set forth below.

In accordance with one embodiment, a guest measurement system includes one or more sensors configured to generate sensor signals indicative of guest characteristics in an attraction measurement area of an individual attraction within a theme park. The guest measurement system includes a controller configured to receive the sensor signals indicative of the guest characteristics from the one or more sensors. The controller includes a processor configured to detect one or more limbs of a guest based in part on the sensor signals. The processor is configured to identify a plurality of subregions for an individual limb of the one or more limbs and to estimate dimensions for the identified plurality of subregions for the individual limb of the one or more limbs and generate a guest height calculation based on the estimated dimensions for the identified plurality of subregions.

In accordance with an embodiment, a method of measuring a guest in an attraction measurement area includes receiving one or more sensor signals indicative of a guest distance from a height marker from one or more sensors. In response to detecting that the guest is within a threshold distance from the height marker, a guest measurement is initiated. The guest measurement includes using the one or more sensor signals to identify limbs of the guest, estimating dimensions of subregions of the identified limbs based on the height marker, and using the estimated dimensions of the subregions to generate a guest height calculation.

In accordance with one embodiment, a guest measurement system includes one or more sensors configured to generate sensor signals indicative of guest characteristics in an attraction measurement area of an individual attraction within a theme park, and a controller configured to receive the sensor signals indicative of the guest characteristics from the one or more sensors. The controller includes a processor configured to identify one or more anatomical features of a guest based in part on the sensor signals, estimate a dimension for the identified one or more anatomical features, and generate a guest height calculation based on the estimated dimension.

In accordance with one embodiment, a guest measurement device includes one or more sensors configured to generate sensor signals indicative of guest characteristics in an attraction measurement area of an individual attraction within an amusement park. The device also includes a controller configured to receive a user input to activate one or more light detection and ranging sensors to emit photons into an area; receive, at the light detection and ranging sensors, reflected photons; generate a sensor signal based on receiving the reflected photons; identify one or more anatomical features of a guest based in part on the sensor signals; estimate a dimension for the identified one or more anatomical features; and generate a guest height calculation based on the estimated dimension.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Presently disclosed embodiments facilitate attraction measurement techniques for measuring one or more guest characteristics that in turn may be used to determine eligibility of the guest to enter a height-restricted attraction. The measurement techniques permit guests to be measured while in a variety of positions, e.g., standing, seated, slouching, or leaning over. Further, the measurement techniques reduce user measurement error or confusion associated with attraction eligibility requirements.

Figure 1:
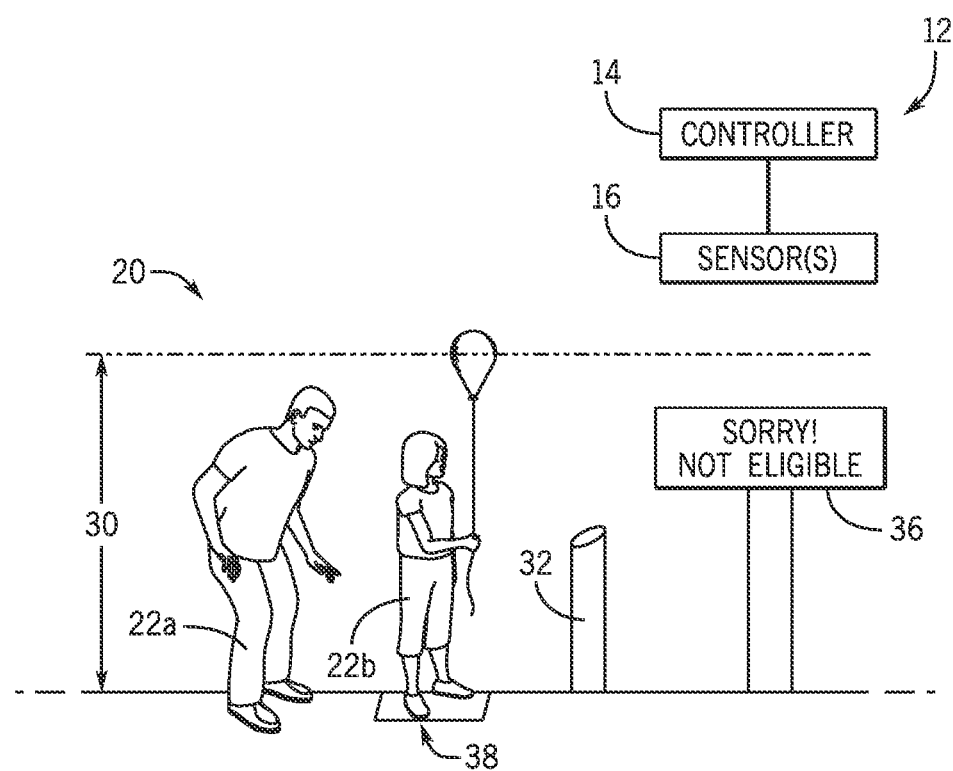
FIG. 1 is a schematic view of an attraction measurement area of an amusement park in accordance with present embodiments.

FIG. 1 shows an example guest measurement system 12 that includes a controller 14 coupled to one or more sensors 16 that generate guest measurement data in a guest measurement area 20 of an attraction. The one or more sensors 16 (e.g., depth sensors) are disposed about the area 20. The one or more sensors 16 may be co-located with one another or disposed separately at distributed locations in the measurement area 20. The one or more sensors may include depth sensors, color sensors, proximity sensors, and the like.

In one embodiment, the depth sensors may include an infrared projector, an infrared camera, and a RGB camera in order to obtain a guest's measurements. The one or more sensors may be co-located with one another or disposed separately at particular locations in the measurement area. For example, the one or more sensors may be disposed on a ceiling of the measurement area 20 or on a nearby wall in order to capture the measurements of the guest and surrounding area. Additionally, a guest-services employee may use a hand-held device containing the one or more sensors 16 in order to obtain measurements by moving the hand-held device in front of the guest to obtain relevant data. In one embodiment, the hand-held device containing the one or more sensors 16 is hand-held mobile device or tablet. The sensor 16 may include a light detection and ranging (LiDAR) capable sensing system. The LiDAR-capable sensing system may be integral with the hand-held mobile device or tablet to permit the hand-held mobile device or tablet to activate measurement at the LiDAR-capable sensing system, receive the measurement data using the LiDAR-capable sensing system, and view the The system may include a vertical-cavity surface-emitting laser, or VCSEL that emits bursts of photons in an area including the guest and that receives a reflected optical signal at the device. Measurement of the photons received at a detector (e.g., single-photon avalanche diodes (SPADs) adjacent to the source can be used to derive the distance of the objects or surfaces from the camera lens. The resolution of the distances can be based on an arrangement of the projection grid of the VCSEL. The device may, in embodiments, include a VCSEL that emits a series of points in the infrared which are detected by a receiver sensor. The LiDAR-capable sensing system can be used to generate depth information for the sensed area, which may lead to more accurate distance determination.

The one or more sensors 16 may also obtain measurements of a known height marker 32 disposed along an axis of a plane of the guest measurement area or known height prop disposed in the measurement area 20 in order to be calibrated, as explained further below.

The guest measurement system 12 permits guests to move naturally in or within the area 20 and may include a marker 38 for the guest to be measured automatically and, in embodiments, without guest input or estimation of their own measurements (e.g., height). The one or more sensors 16 collect environmental data that includes data representative of one or more guests, illustrated as a first guest 22a and a second guest 22b in FIG. 1. The environmental data is provided to the controller 14, which uses the environmental data to determine a guest characteristic, such as height. The guest measurement system 12 permits guests to be accurately measured while leaning over or seated, e.g., in a wheelchair or a stroller. As shown by way of example, the first guest 22a is taller than the second guest 22b. However, the first guest 22a is leaning over, while the second guest 22b is holding a balloon. If a distance 30 from the ground represents the minimum height to ride an attraction, an optical beam type sensor that measures beam disruptions at the minimum height would mistakenly indicate the second guest 22b as being tall enough, because the balloon would break the beam. Further, the first guest 22a would also be incorrectly identified as being not tall enough. In contrast, the disclosed measurement system 12 as provided herein would correctly identify the first guest 22a as being tall enough and the second guest 22b as not being at least the minimum height. The system 12 uses sensor signals to identify anatomical features and generate a height calculation based on estimated dimensions of the anatomical features. In embodiments, the system 12 may provide a display 36 or other indicator to indicate qualifying or not qualifying height calculations.

In an embodiment, using the information obtained via the one or more sensors 16, one or more guest features are identified. The guest features may be an anatomical feature, e.g., each of the guest's limbs are identified. The guest's head, neck, torso, pelvis, arms, knees, shins, ankles, feet, hands, toes, fingers, and so forth may be identified. It may be appreciated that some of these limbs may have a paired limb or corresponding limb across a medial axis of the guest's body (i.e., a right limb and a left limb). The presently disclosed embodiments include identifying a plurality of subregions for each of the identified anatomical features (e.g., limbs) and estimating a measurement or dimension of each of the plurality of subregions. The total height of the guest may be estimated or calculated by summing certain subregion measurements to obtain a limb estimate. For example, an estimated total leg height may be based on summing certain leg subregions. In an embodiment, the leg height plus the guest torso height and head dimensions may be used to determine guest height. In another embodiment, a guest's wing span can be used to determine that a guest's height has been calculated correctly. For example, the wing span may be generally defined as the length from one end of an individual's arms to the other when raised parallel to the ground at shoulder height at 90 degrees. The height of a human is generally about that of the wing span, which can serve as a quality check to confirm the estimated height of the guest.

Various mathematical relationships and equations (e.g., 3D Pythagorean theorem, linear interpolation) may be used to estimate the height of a particular subregion. It may be appreciated that a measurement of a particular subregion of a first limb may be substituted for a second corresponding limb, when a confidence level associated with the first limb exceeds that of the second corresponding limb by more than a threshold (e.g., more than one standard deviation). The presently disclosed embodiments include generating an overall height calculation of the guest based on the estimated limb measurements. In this way, the guest may remain seated (e.g., in a wheelchair) while being measured prior to accessing the ride.

Figure 2:
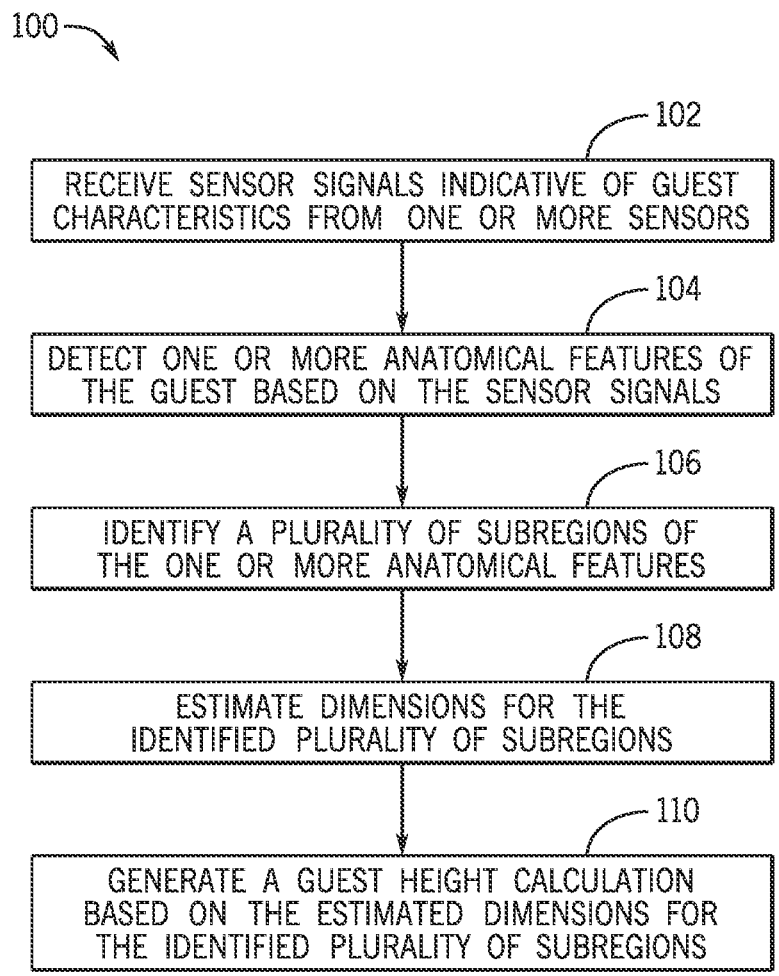
FIG. 2 is a flow diagram of a method using a guest measurement system in accordance with present embodiments.

With the foregoing in mind, FIG. 2 is a flow diagram of a method 100 using a guest measurement system in accordance with present techniques. The method 100 includes receiving (block 102) sensor signals indicative of guest characteristics, e.g., depth sensor information, from one or more sensors disposed in a measurement area before boarding a ride.

The method 100 includes detecting (block 104) anatomical features, e.g., one or more limbs, of a guest based on the information obtained from the one or more sensors. It may be appreciated that the sensor information obtained from the one or more sensors may first be filtered, normalized, calibrated, and/or pre-processed to be used more readily with a height calculation logic as provided herein. A presence and a position of various limbs and/or anatomical features of the guest, including the guest's head, neck, torso, pelvis, thigh, knee, calf, shin, ankle, foot, toe, hand, wrist, finger, elbow, forearm, and so forth may be identified or detected based on the sensor information. Skeletal tracking may be used to predict or observe the position of anatomical joints within a guest's body. The positions will be used to create a data structure from which the distances between joints can be calculated and visualized on a screen. Adding the lengths between the identified joints can be used to estimate height. In an embodiment, the techniques may be used to identify a limb difference, such as an amputation and the length of identified amputation. Based on stored attraction information, a notification can be generated for attractions that the guest is eligible to ride. The system may use depth sensors to create an image of skeletal structure of an individual within a 3D space in real-life coordinates. Multiple depth sensors can be used to create a composite image in 3D space that can reinforce the data collected.

The method 100 includes identifying a plurality of subregions for an individual limb (block 106). For example, the method 100 may use various mathematical equations and relationships (e.g., geometry, a 3D Pythagorean theorem, linear interpolation) in order to estimate one or more dimensions of a particular subregion. It may be appreciated that the limbs may be divided into subregions for purposes of estimating their dimensions. For example, a left calf of the guest may be measured in three subregions, while corresponding measurements of the corresponding three subregions on a right calf of the guest may be measured. By doing so, the guest measurement system may be able to better estimate the overall height of the guest by using the most accurate measurements for a particular subregion, whether the measurement used is from the left calf of the guest or the right calf of the guest, as explained further below with reference to FIG. 5. The estimated dimensions may include a length estimate between joints (e.g., wrist-to-elbow; elbow-to-shoulder, ankle-to-knee, knee-to-hip) and/or a width estimate in a plane parallel to a length axis.

That is, an overall limb measurement or dimensions may be estimated (block 108) by using some measurements from a left limb and some measurements from a right limb. An accuracy of the estimations for each of the limbs may also be determined. In order to determine a certainty of the estimated dimensions of each subregion of each limb, the guest measurement system may perform a calibration to compare to a measurement obtained by the one or more sensors to those with a calibration standard, such as the height of the known height marker or the known height prop. A statistical analysis may be performed to identify outliers in the estimates. In some embodiments, the measurements falling outside of a threshold (e.g., one standard deviation, two standard deviations) may be removed from the subregion measurements in order to improve an accuracy of the overall height calculation.

The method 100 includes generating (block 110) an overall guest height calculation for the guest based on combinations of the estimated limb subregions. When there is more than one measurement for a particular subregion (e.g., a subregion of a left thigh vs. a subregion of a right thigh), the guest measurement system may then determine which measurement for the particular subregion has a higher degree of certainty associated with it and use the more certain measurement. Once each of the subregions of the limbs are estimated, the method includes generating the final height calculation. By using the method described herein, the guest may be measured to determine whether he can enter the ride without having to stand up from a wheelchair, assisted mobility device, stroller, and so forth. Further, it may be appreciated that the techniques described herein may also be applied to a guest that does not have any movement restrictions.

Figure 3:
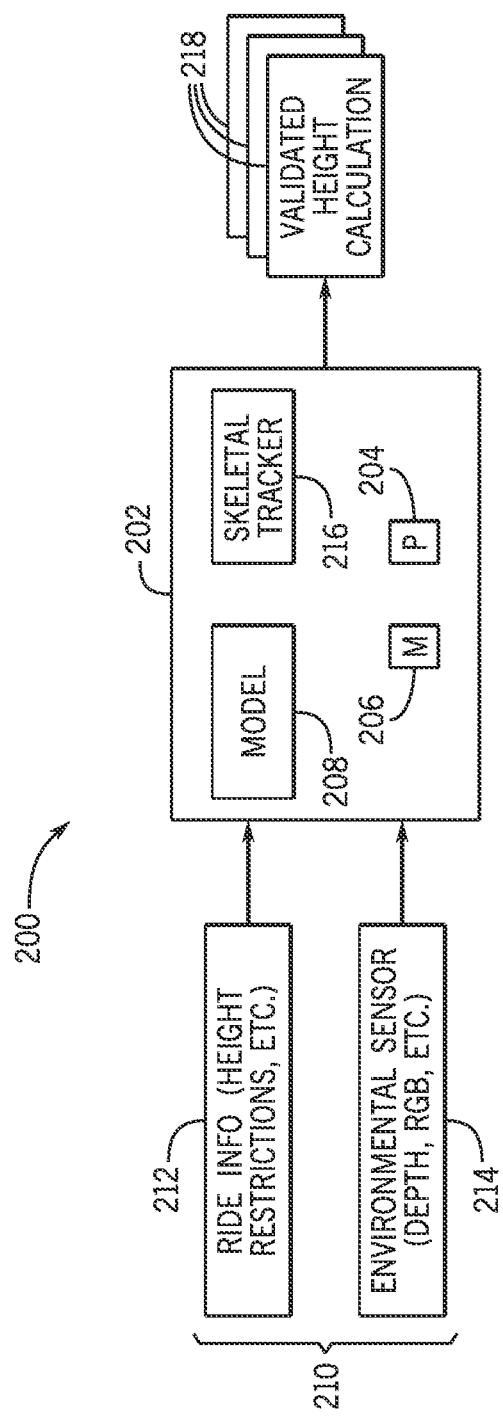
FIG. 3 is a block diagram of a guest measurement system in accordance with present embodiments.

FIG. 3 is a block diagram of a guest measurement system 200 in accordance with present embodiments. The guest measurement system 200 includes a controller 202 that may be implemented in a computing device, a server, a distributed processor, or a cloud computing environment. The controller 202 includes a processor 204 and a memory 206. The processor 204 may include one or more processing devices (processing or computing circuitry), and the memory 206 may include one or more tangible, non-transitory, machine-readable media. By way of example, such machine-readable media can include RAM, ROM, EPROM, EEPROM, or optical disk storage, magnetic disk storage or other magnetic storage devices, or any other medium which can be used to carry or store desired program code in the form of machine-executable instructions or data structures and which can be accessed by the processor 204 or by other processor-based devices (e.g., mobile devices). The controller 202 may utilize one or more types of models 208 (e.g., software-based models executable by the processor 204). For example, the models 208 may include geometry-based models, such as a 3-D Pythagorean Theorem model. Association techniques may be used to find relationship between variables. In one embodiment, a skeletal tracker 216 may establish a presence and/or a position of various skeleton joints and/or anatomical features, such as a the guest's head, hands, torso, center of mass, pelvis/hips, thighs, knees, shins, ankles, feet, and so forth.

The model 208 may receive various inputs 210 in order to perform estimations for each subregion of the guest's limbs. The inputs 210 may include ride information 212 and depth data 214. The ride information 212 may include restrictions for a particular ride. For example, the ride may have particular height or weight limitations. Additionally, certain ride seats may only accommodate a certain depth for a passenger, and thus, a guest with certain disability equipment (e.g., a cane, a wheelchair, etc.) may not be able to go on the ride, may require the use of an additional seat (e.g., adjacent seats), or may require a particular seat on the ride that is suitable for the guest.

The depth data 214 may include data from one or more sensors. The one or more sensors may be disposed on a ceiling or a wall of an attraction measurement room or may be disposed in a hand-held device that is operated by a team member. The one or more sensors may include depth sensors, color sensors, proximity sensors, and the like. In one embodiment, the depth sensors may include an infrared projector, an infrared camera, and a RGB camera in order to obtain a guest's measurements. The infrared projector, the infrared camera, and the RGB camera may be disposed in close proximity to each other (e.g., within a few centimeters of one another) or co-located with one another. As may be appreciated, the infrared projector may project infrared light patterns on nearby objects in the area, which are detected by the infrared camera. The infrared camera and/or the RGB camera capture the projected infrared light patterns. The cameras then send the video of the captured infrared light pattern to the depth sensor processor to determine the depth of each of the projected infrared light patterns (e.g., dots). In one embodiment, density of the projected infrared light pattern on a particular object can be correlated to distance from the projector. In an embodiment, the depth sensors may include a LiDAR sensing system that generates the depth data 214.

Returning now to the discussion of the model 208, the model 208 uses various mathematical equations and relationships (e.g., geometry, a 3D Pythagorean theorem, linear interpolation) in order to estimate a height or length of a particular subregion of a particular identified limb. The identified limbs may be divided into a number of subregions, based in part on a size of the limb, a certainty of the particular identified limb, and so forth. Certain limbs may be present on either side of a medial axis of the body that divides the guest's body into left and right sides. When an identified limb has a paired limb (i.e., a left shin on the left side of the body and a right shin on the right side of the body), the model 208 may estimate the height of both the left and the right limb, but only use the estimate for one limb if the left limb and the right limb are deemed to be sufficiently similar in size. In this instance, the model 208 may use the estimated height of only one limb (i.e., the left shin or the right shin) after determining which of the estimations is more accurate based on the depth data 214. However, if the model 208 determines that the left and the right limb are outside of a particular threshold of similarity, the model 208 may use the estimate of the height of both of the left and the right limb. In another embodiment, the model 208 estimates and uses the height of both of the paired limbs, regardless of a threshold of similarity.

In one embodiment, the model 208 determines the height or the length of corresponding subregions for paired limbs. For example, the model 208 may determine the height or the length of a first region, a second region, and a third region of the guest's left calf. The model 208 may also determine the height or the length of a corresponding first region, a corresponding second region, and a corresponding third region of the guest's right calf. The model 208 then determines whether the first region of the left calf or the corresponding first region of the right calf is more accurate, based on a certainty of the depth data 214 provided from the region. The model 208 may then use the more accurate measurement to proceed with generating the overall height calculation. Indeed, the model 208 may use measurements from a particular subregion of either side of the body for one particular limb, in order to improve accuracy.

In order to determine a certainty of the estimated height of each subregion of each limb, the controller 202 may perform a calibration to compare to a measurement obtained by the one or more sensors to those with a calibration standard, such as the height of the known height marker or the known height prop. The controller 202 may then determine whether the certainty of the measured height of each subregion or limb is acceptable (e.g., within a determined acceptable error). When there is more than one measurement for a particular subregion (e.g., a subregion of a left thigh vs. a subregion of a right thigh), the controller 202 may then determine which measurement for the particular subregion has a higher degree of certainty associated with it and use the more certain measurement.

The model 208 may then use the more accurate measurement for the particular region in order to output a validated height calculation 218 for the particular region. Once the controller 202 has determined the validated height calculation 218 for each of the particular regions, an overall validated height calculation may be generated. The controller 202 may output the overall validated height calculation of the guest's entire body by summing each of the validated height estimations of each limb. The final validated height calculation may be used to determine whether the ride has sufficient space to accommodate the guest while the guest remains seated or assisted by the guest's assistive equipment (e.g., in the guest's wheelchair, assisted mobility device, stroller) without requiring the guest to disembark from the guest's assistive equipment. In an embodiment, the output may include a notification regarding eligibility to ride a particular attraction based on the estimated height.

Figure 4:
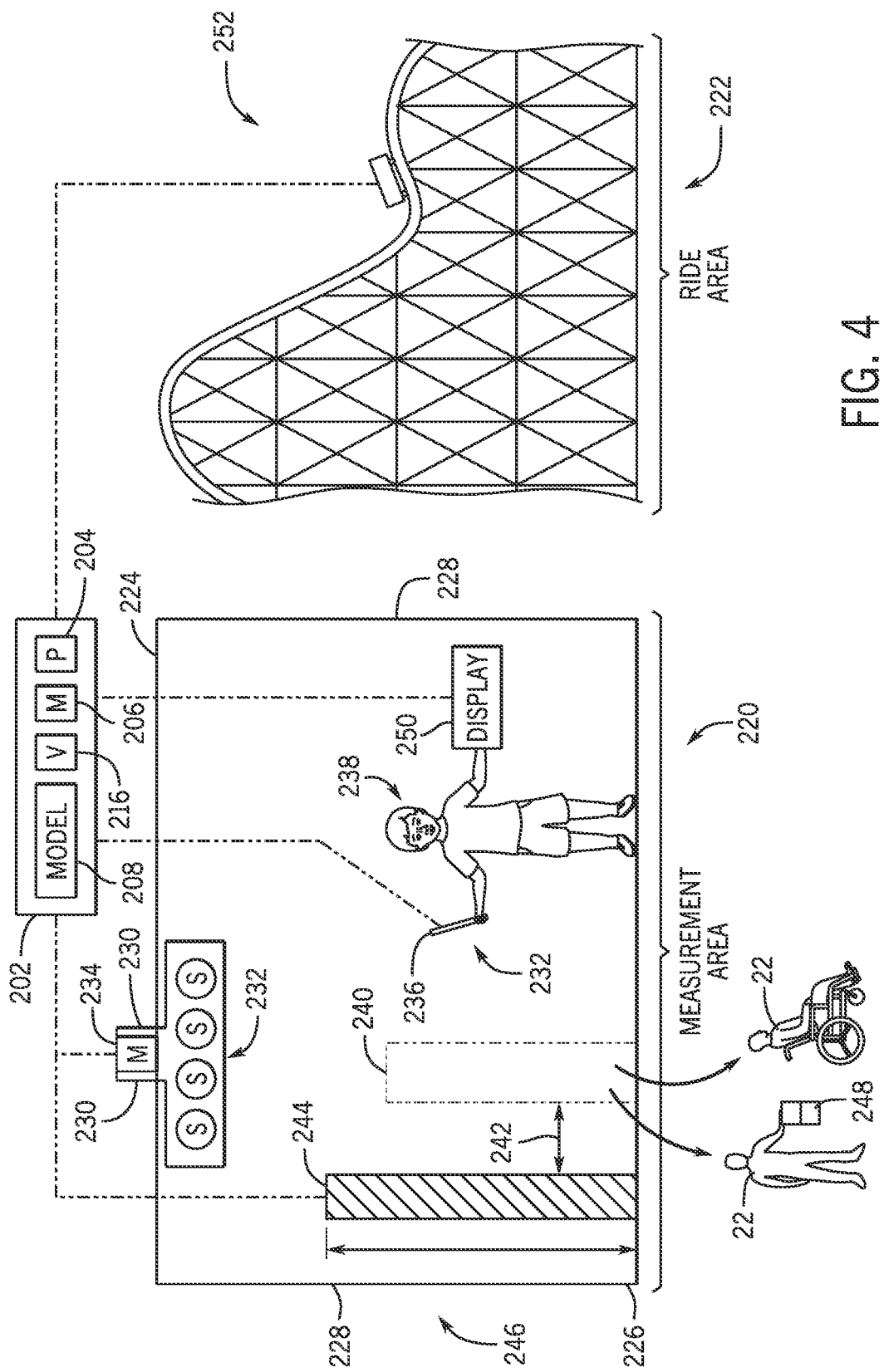
FIG. 4 is a schematic view of an attraction measurement area of the amusement park utilizing the guest measurement system in accordance with present embodiments.

FIG. 4 is a schematic of a side view of an attraction measurement area of the theme park utilizing the guest measurement system 200 of FIG. 3 in accordance with present embodiments. In the illustrated embodiment, the guest 22 is able to be measured in the attraction measurement area 220 that is a separate enclosed room that is adjacent to the ride area 222. The separate enclosed room may include a ceiling 224, a floor 226, and a plurality of walls 228 to enclose the measurement area. The attraction measurement area may include one or more sensors 232 within the attraction measurement area 220. The one or more sensors 232 can be moved via a motor 234 that is communicatively coupled to a controller 202 in order to adequately capture the image data. Additionally or alternatively, the one or more sensors 232 can be disposed in a hand-held device 236 (e.g., a wand, a tablet, or a mobile device). The hand-held device 236 may be used by a park employee 238 to capture the image data and/or the depth data 214 when the hand-held device 236 is positioned in front of the guest 22.

It may be appreciated that the guest 22 may be asked to move into a space 240 so that the guest 22 may be measured. The space 240 may be a distance 242 away from a height marker 244. The space 240 may be an area where the space 240 can be readily viewed via the one or more sensors 232 that are disposed above the space 240 (e.g., along the rail 230 disposed along the ceiling 224 or via the hand-held device 236 held by the park employee). The height marker 244 may be a particular marker or a prop with a known height that is located the distance 242 behind the space 240. The height marker 244 may be disposed substantially parallel to an axis 246, where the axis 246 may be defined as the axis extending between the ceiling 224 and the floor 226. When the guest 22 is determined to be in position, the height measurement can be initiated. In certain embodiments, the positioning of the guest within a threshold distance to the height marker 244 permits the sensor data to be calibrated to known measurements or dimensions of the height marker 244. Once calibrated, the sensor data is then used to estimate dimensions of the anatomical features.

In embodiments, the sensors 232 are housed in a mobile device or tablet, and an operator activates the sensors 232 via interaction with a user interface of the mobile device or tablet.

It may be appreciated that the guest measurement system 200 may be used to measure the guests 22 that are in a wheelchair, an assisted mobility device, a stroller, a cart, and so forth, or any time the guest 22 is holding an accessory 248 (e.g., a cane, a shopping bag, a purse) that may partially obstruct the view of the guest 22. In the illustrated embodiment, the guest measurement system 200 may be used to measure the guest 22 in a wheelchair. When the guest 22 is in a wheelchair or a stroller, it may be appreciated that a portion of the guest's body may be obstructed from view of the one or more sensors 232. For example, a view of the guest's left leg may be obstructed by a component of the wheelchair. In this instance, the one or more sensors 232 may be unable to adequately capture the dimensions of the guest's left leg. As explained in further detail below, the guest measurement system 200 may then take one or more corrective actions, including but not limited to, attempting to re-measure the left leg, estimating the measurements of the left leg based on other body part measurements, substituting the measurement of the right leg, or a combination thereof. It may be appreciated that the guest measurement system 200 may refer to a database of previously acquired guest measurements to estimate the measurements of the guest. Similar corrective actions may be taken in an instance where a view of the guest's body is obstructed by a stroller, a shopping cart, a shopping bag, and so forth.

The controller 202 may be communicatively coupled to a display 250, the one or more sensors 232, the height marker 244 and/or a nearby ride 252. As discussed above, the controller 202 may receive various inputs 210 in order to adequately estimate the height of each subregion of the guest's limbs. The inputs 210 may include ride information 212, depth data 214, and the like of FIG. 3. The ride information 212 may include a number of available seats, a number of seats that can accommodate guests in an assisted mobility vehicle, restrictions about which types of assisted mobility vehicles are suitable for the particular ride, height restrictions, and weight restrictions, among others. The depth data 214 may be received from the one or more sensors 232 disposed throughout the attraction measurement area. The depth data 214 may be obtained from infrared light patterns that are projected onto objects (e.g., the guest) by one or more infrared light projectors. The one or more infrared cameras may then detect the projected light patterns to determine a depth associated with the object that the pattern is detected on. Both of the various inputs 210 are then input into the model 208 in order to estimate the height of a particular subregion of an identified limb, as discussed above. The estimated height for the guest may be output to the display 250 in order to let the park employee know whether the guest 22 can be accommodated on the ride 252.

In certain embodiments, the disclosed guest measurement system 200 may use facial recognition or other guest tracking techniques to correlate a guest to a measured height. Thus, the guest may be measured at an earlier point in the day, and the estimated height logged to the guest profile. Using guest recognition techniques, the recognized guest can be associated with their estimated height using the guest profile at other attractions to determine ride eligibility. In this manner, the measurement need only occur once during the day.

Figure 5:
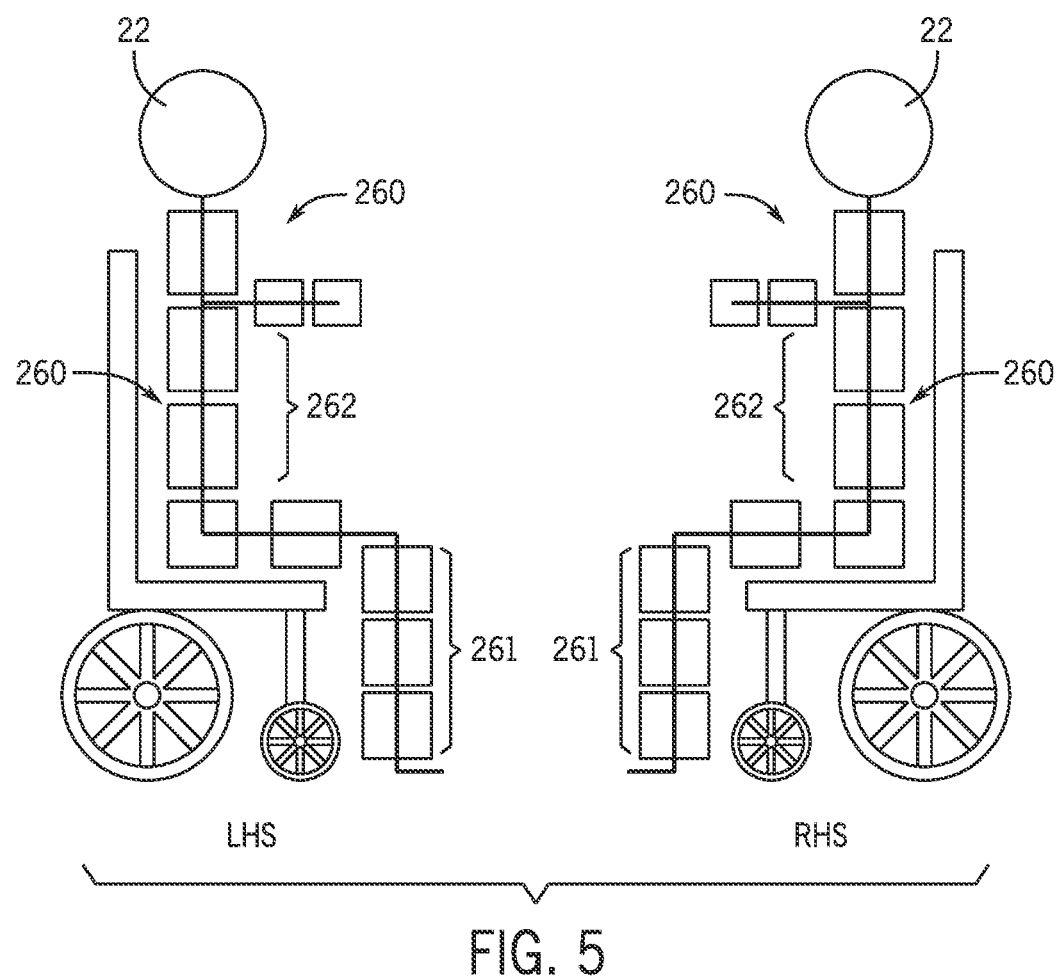
FIG. 5 is a schematic view of a plurality of subregions of various limbs of the guest that are utilized as part of height calculation logic of the guest measurement system, in accordance with present embodiments.

FIG. 5 is a schematic view of a plurality of subregions 260 of various limbs of the guest 22 that are utilized in the guest measurement system, in accordance with present embodiments. It may be appreciated that each of the identified limbs may be split into various subregions for purposes of gathering the depth information. In some embodiments, the paired limbs (e.g., a left shin and a right shin) may be split into a varying number of subregions depending on a size of the limb. For example, the limb of a larger guest (e.g., having a longer shin) may be split into four subregions, whereas the limb of an average sized guest (e.g., having an average length shin 261) may be split into only three subregions. Though certain anatomical features will not have pairs (e.g., a torso, a neck), the same concept of applying a varying number of subregions to the identified limb may apply. In the illustrated embodiment, though the torso 262 of the guest 22 is split into two subregions, the depth information for the torso may be obtained over three, four, or more subregions for a larger guest.

As discussed above, the guest measurement system 200 of FIG. 3 may receive depth information from the one or more sensors 232 of FIG. 4. The guest measurement system 200 may receive multiple depth information readings for a given subregion from various sensors disposed in the attraction measurement area 220 of FIG. 4. For example, for the particular subregion 260 (i.e., the torso 262), the guest measurement system 200 may receive depth information from the one or more sensors 232 located above the space 240 of FIG. 4, on the adjacent walls 224, 228 of FIG. 4, and/or from the hand-held device 236 of FIG. 4. It may be appreciated that though the guest measurement system 200 receives depth information for the same particular subregion from the various sensors 232, the depth information from each sensor 232 may remain siloed. In this way, if the depth information received from a single sensor 232 appears to be erroneous (e.g., outside an acceptable measure of uncertainly), the guest measurement system 200 may discount the erroneous depth information when estimating the length of the particular limb.

In some embodiments, the guest measurement system 200 may receive multiple depth information measurements for each subregion 260. The guest measurement system 200 may then determine whether any of the collected depth information includes one or more outliers for the particular subregion. When the guest measurement system 200 determines a presence of any statistical outliers, the outliers may be excluded from the collected depth information used to estimate the height of the particular subregion 260. When the guest measurement system 200 determines that one or more outliers are present, one or more corrective actions may be implemented. The one or more corrective actions may be implemented in place of or in addition to excluding the outlier. As discussed above, the one or more corrective actions may include, but are not limited to, attempting to re-measure the particular subregion 260 of the identified limb, estimating the measurements of the particular subregion 260 of the identified limb based on other body part measurements (e.g., estimating the measurement of the particular subregion 260 of the identified limb based on a database), or substituting the measurement of the paired subregion 260 of the identified limb.

For example, it may be appreciated that the guest measurement system 200 may re-calibrate the one or more sensors 232 in the event that one or more outliers is identified. Re-calibration of the one or more sensors 232 may include comparing a measurement obtained by the one or more sensors 232 to those with a known standard, such as the height of the known height marker 244, or another suitable calibration technique. In another non-limiting example, the corrective action may include estimating the measurement of the particular subregion of the identified limb based on measurements obtained from a historical database. As such, the guest measurement system 200 may substitute one or more measurements from the historical database by identifying suitable subregion measurements based in part on the guest's overall height and stature, whether the guest is sitting or standing, a particular model of an assisted mobility vehicle (e.g., wheelchair, stroller), and the like.

In another non-limiting example, the guest measurement system 200 may use subregions having higher quality measurements and may discard or not use subregions having lower quality measurements. Thus, the measurement or estimate of the guest limb length may be based on a summation of individual subregions from different corresponding limbs. In one example, a leg measurement may be based on a summation of a left shin and a right thigh region if those subregions represent the highest quality subregions for the legs. The quality metric may be based on the confidence of the raw sensor data. For example, the guest measurement system 200 may substitute sensor data for a subregion of a left shin with a corresponding subregion of a right shin, when the sensor data for the right shin is identified as an outlier outside of the desired confidence interval. In this case, the guest measurement system 200 may disregard the data for the subregion of the left shin when generating the overall height calculation for the guest 22.

While only certain features of the present embodiments have been illustrated and described herein, many modifications and changes will occur to those skilled in the art. It is, therefore, to be understood that the appended claims are intended to cover all such modifications and changes as fall within the true spirit of the present disclosure. Further, it should be understood that certain elements of the disclosed embodiments may be combined or exchanged with one another.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

The invention claimed is:

1. A guest measurement system, comprising:
one or more sensors configured to generate sensor signals indicative of guest characteristics in an attraction measurement area of an individual attraction within an amusement park;
a controller configured to receive the sensor signals indicative of the guest characteristics from the one or more sensors, the controller comprising a processor configured to:
detect one or more limbs of a guest based in part on the sensor signals;
identify a plurality of subregions for an individual limb of the one or more limbs;
estimate dimensions for the identified plurality of subregions for the individual limb of the one or more limbs;
generate a guest height calculation based on the estimated dimensions for the identified plurality of subregions; and
select a ride seat for the guest based in part on the guest height calculation.

2. The guest measurement system of claim 1, wherein the one or more sensors comprises a camera or a depth sensor.

3. The guest measurement system of claim 1, wherein the processor is configured to detect the one or more limbs of the guest by determining a right side limb and a corresponding left side limb of a same type.

4. The guest measurement system of claim 3, wherein the processor is configured to:
determine a first confidence interval of first estimated dimensions for the right side limb and a second confidence interval of second estimated dimensions for the corresponding left side limb; and
determine that the first confidence interval or the second confidence interval exceeds a threshold.

5. The guest measurement system of claim 4,
wherein the processor is configured to, upon determining that the first confidence interval exceeds the threshold and the second confidence interval does not exceed the threshold, use the first estimated dimensions for subregions of the right side limb and not the second estimated dimensions for subregions of the corresponding left side limb for determining the guest height calculation.

6. The guest measurement system of claim 1, wherein the processor is configured to determine a length dimension of a length between joints of the one or more limbs.

7. The guest measurement system of claim 1, wherein the one or more limbs comprise a leg or an arm.

8. The guest measurement system of claim 1, wherein the processor is configured to generate an indication that the guest is qualified for the individual attraction based in part on the guest height calculation.

9. The guest measurement system of claim 1, wherein the sensor signals generate a signal indicative of one or more dimensions of a height marker in the attraction measurement area.

10. A method of measuring a guest in an attraction measurement area comprising:
receiving one or more sensor signals indicative of a guest distance from a height marker from one or more sensors; and
in response to detecting that the guest is within a threshold distance from the height marker, initiating a guest measurement, wherein the guest measurement comprises using the one or more sensor signals to identify limbs of the guest, estimating dimensions of subregions of the identified limbs based on the height marker, and using the estimated dimensions of the subregions to generate a guest height calculation.

11. The method of claim 10, comprising:
detecting that the guest distance exceeds the threshold distance from the height marker; and
outputting an indication that the guest is not located within the threshold distance.

12. The method of claim 10, wherein the height marker is disposed along an axis of a plane of the attraction measurement area, and wherein the height marker comprises an object of a known height.

13. The method of claim 12, comprising:
summing a portion of the subregions of the identified limbs to generate a limb measurement and generating the guest height calculation based on the limb measurement.

14. The method of claim 10, wherein the one or more sensors comprises a camera.

15. A guest measurement system, comprising:
one or more sensors configured to generate sensor signals indicative of guest characteristics in an attraction measurement area of an individual attraction within an amusement park; and
a controller configured to receive the sensor signals indicative of the guest characteristics from the one or more sensors, the controller comprising a processor configured to:
identify one or more anatomical features of a guest based in part on the sensor signals;
estimate a dimension for the identified one or more anatomical features;
generate a guest height calculation based on the estimated dimension;
store the guest height calculation as part of a guest profile of the guest;
identify the guest based on guest tracking information;
access the guest profile of the identified guest; and
generate indications of ride eligibility at a plurality of rides using the stored guest height calculation of the guest profile, wherein the guest height calculation occurs once for the plurality of rides over a period of time.

16. The guest measurement system of claim 15, wherein the processor is configured to:
identify a plurality of subregions for an individual anatomical feature of the identified one or more anatomical features.

17. The guest measurement system of claim 16, wherein the processor is configured to:
estimate dimensions for the identified plurality of subregions of the individual anatomical feature.

18. A guest measurement device, comprising:
one or more sensors configured to generate sensor signals indicative of guest characteristics in an attraction measurement area of an individual attraction within an amusement park; and
a processor configured to:
receive a user input to activate one or more light detection and ranging sensors to emit photons into an area;
receive, at the light detection and ranging sensors, reflected photons;
generate a sensor signal based on receiving the reflected photons;
identify one or more anatomical features of a guest based in part on the sensor signals;
estimate a dimension for the identified one or more anatomical features; and
generate a guest height calculation based on the estimated dimension.

19. The guest measurement system of claim 15, wherein the processor is configured to:
identify the guest based on guest tracking information;
access the guest profile of the identified guest; and
generate an indication of ride eligibility for the identified guest using the stored guest height calculation of the guest profile.

20. The guest measurement device of claim 18, wherein the processor is configured to:
identify a plurality of subregions for an individual anatomical feature of the identified one or more anatomical features.

21. The guest measurement device of claim 20, wherein the processor is configured to:
estimate dimensions for the identified plurality of subregions of the individual anatomical feature.

\* \* \* \* \*